(12) United States Patent
Tanaka et al.

(10) Patent No.: US 7,417,187 B2
(45) Date of Patent: Aug. 26, 2008

(54) COMPOSITE CABLE AND COMPOSITE CABLE PROCESSED PRODUCT

(75) Inventors: Masato Tanaka, Aomori (JP); Kazuhiro Sato, Tochigi (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 11/652,146

(22) Filed: Jan. 11, 2007

(65) Prior Publication Data

US 2007/0184689 A1    Aug. 9, 2007

(30) Foreign Application Priority Data

Jan. 13, 2006    (JP) .............................. 2006-005494

(51) Int. Cl.
*H02B 1/40* (2006.01)
(52) U.S. Cl. ....................... 174/47; 174/113 R; 174/116
(58) Field of Classification Search ................... 174/47, 174/113 C, 131 A, 116, 113 R
See application file for complete search history.

(56) References Cited

U.S. PATENT DOCUMENTS

| | | | | |
|---|---|---|---|---|
| 2,578,280 A | * | 12/1951 | Barnard | 174/95 |
| 3,281,571 A | * | 10/1966 | Gilmore | 219/137.9 |
| 3,483,313 A | * | 12/1969 | Schaffhauser | 174/101.5 |
| 3,529,632 A | * | 9/1970 | Johns | 138/111 |
| 5,902,958 A | * | 5/1999 | Haxton | 174/47 |
| 6,538,198 B1 | * | 3/2003 | Wooters | 174/47 |

FOREIGN PATENT DOCUMENTS

| | | |
|---|---|---|
| EP | 0 782 125 A2 | 7/1997 |
| EP | 1 652 476 A2 | 5/2006 |
| JP | 2003-38485 | 2/2003 |
| JP | 2005-27737 A | 2/2005 |

OTHER PUBLICATIONS

Austrian Office Action issued in Corresponding Austrian Patent Application No. 3A A 41/2007 - 1 dated on Jul. 23, 2007.

* cited by examiner

*Primary Examiner*—Chau N Nguyen
(74) *Attorney, Agent, or Firm*—McDermott Will & Emery LLP

(57) ABSTRACT

A composite cable includes at least two flexible resin tubes through which a refrigerant flows, and a plurality of signal lines or a plurality of signal line units including a plurality of signal lines. The plurality of signal lines or the plurality of signal line units is disposed annularly around the resin tubes.

7 Claims, 2 Drawing Sheets

COMPOSITE CABLE AND COMPOSITE CABLE PROCESSED PRODUCT

The present invention claims priority from Japanese patent application no. 2006-005494 filed on Jan. 13, 2006, the entire content of which is incorporated herein by reference.

BACKGROUND OF THE INVENTION

1. Field of the Invention

The present invention relates to a composite cable used for transmitting electric signals from an ultrasonic probe etc. More specifically, the present invention relates to a composite cable having a refrigerant pipe, and a composite cable processed product using such a composite cable.

2. Description of the Related Art

An inspection device using an ultrasonic wave is utilized, for example, in a tomographic inspection in a medical field or in a defect inspection of various structural objects. Such inspection devices that use ultrasonic waves conduct a kind of image inspection method in which an internal state of a target object is inspected in a nondisruptive manner by applying ultrasonic waves to the target object and converting the reflected ultrasonic waves into images. Especially in the medical field, since it is possible to observe a motion of each soft tissue in real time without a radiation exposure, such inspection devices are frequently used.

Such a medical inspection method using ultrasonic waves is an inspection method in which an ultrasonic probe having a piezoelectric vibrator is applied to a human body, ultrasonic waves are irradiated, and the ultrasonic reflected waves are received. The piezoelectric vibrator is disposed inside a tip portion of the ultrasonic probe where a human body is to be applied. A transmitting and receiving circuit is also disposed in the vicinity of the tip portion of the ultrasonic probe so as not to be affected by noises. Therefore, a temperature of a portion where the piezoelectric vibrator is disposed may become high, whereby a patient may suffer from burns or an operator may have trouble in handling. Recently, higher performance and higher function are expected, and when a multi-channelization proceeds, a heating value at the tip portion of the ultrasonic probe becomes larger.

Therefore, there is a problem in that a sufficient heat radiation cannot be obtained only by heat radiating to a rear side of the ultrasonic probe with a heat conducting member. In order to improve the heat radiation, there has been proposed a configuration in which a cooling jacket is wound around the ultrasonic probe, and refrigerant is circulated in the cooling jacket, thereby coercively cooling the ultrasonic probe (see, e.g., JP-A-2005-027737).

In the cooling configuration disclosed in JP-A-2005-027737, a flexible circulation tube is used for circulating the refrigerant through the cooling jacket, and the circulation tube is clamped along a signal cable for transmission to and reception from the ultrasonic probe. In an application of an ultrasonic inspection device, good handling ability is required. However, since the circulation tube disclosed in JP-A-2005-027737 is provided separately from the signal cable, the handling ability is not good. In addition, even if the circulation tube and the signal cable are simply integrated in a composite manner, there are problems in that an insulation coating of the signal cable may be adversely affected by a dew condensation that is likely to be generated on an outer surface of the circulation tube through which the refrigerant flows, and in that bending property etc. need to be considered.

SUMMARY OF THE INVENTION

It is an object of the present invention to provide a composite cable and a composite cable processed product, in which a number of signal lines and refrigerant circulation tubes are integrated so as to have a good handling ability, with less influence of a dew condensation due to a circulation of a refrigerant, and without deterioration of bending property or shield property.

According to one aspect of the invention, a composite cable includes at least two flexible resin tubes through which a refrigerant flows, and a plurality of signal lines or a plurality of signal line units including a plurality of signal lines. The plurality of signal lines or the plurality of signal line units is disposed annularly around the resin tubes.

According to another aspect of the invention, the composite cable may further include a heat insulating member, and a heat insulating tape that is wound around an outer periphery of the resin tubes and the heat insulating member.

According to another aspect of the invention, the composite cable may further include a wrapping tape, and a common shield conductor. The plurality of signal lines or the plurality of signal line units is assembled around the resin tubes, and is wrapped with the wrapping tape. The common shield conductor is formed around an outer periphery of the wrapping tape.

According to another aspect of the invention, a composite cable processed product includes the composite cable described in the above aspects of the invention, and a component such as an electric connector or a circuit substrate. The plurality of signal lines or the plurality of signal line units is connected to the component at a terminal portion of the composite cable, and at least two of the resin tubes are coupled at the terminal portion of the composite cable. The composite cable processed product may further include a connecting tube, and at least two of the resin tubes may be coupled at the terminal portion of the composite cable via the connecting tube.

DESCRIPTION OF THE EXEMPLARY EMBODIMENT

Figure 1:
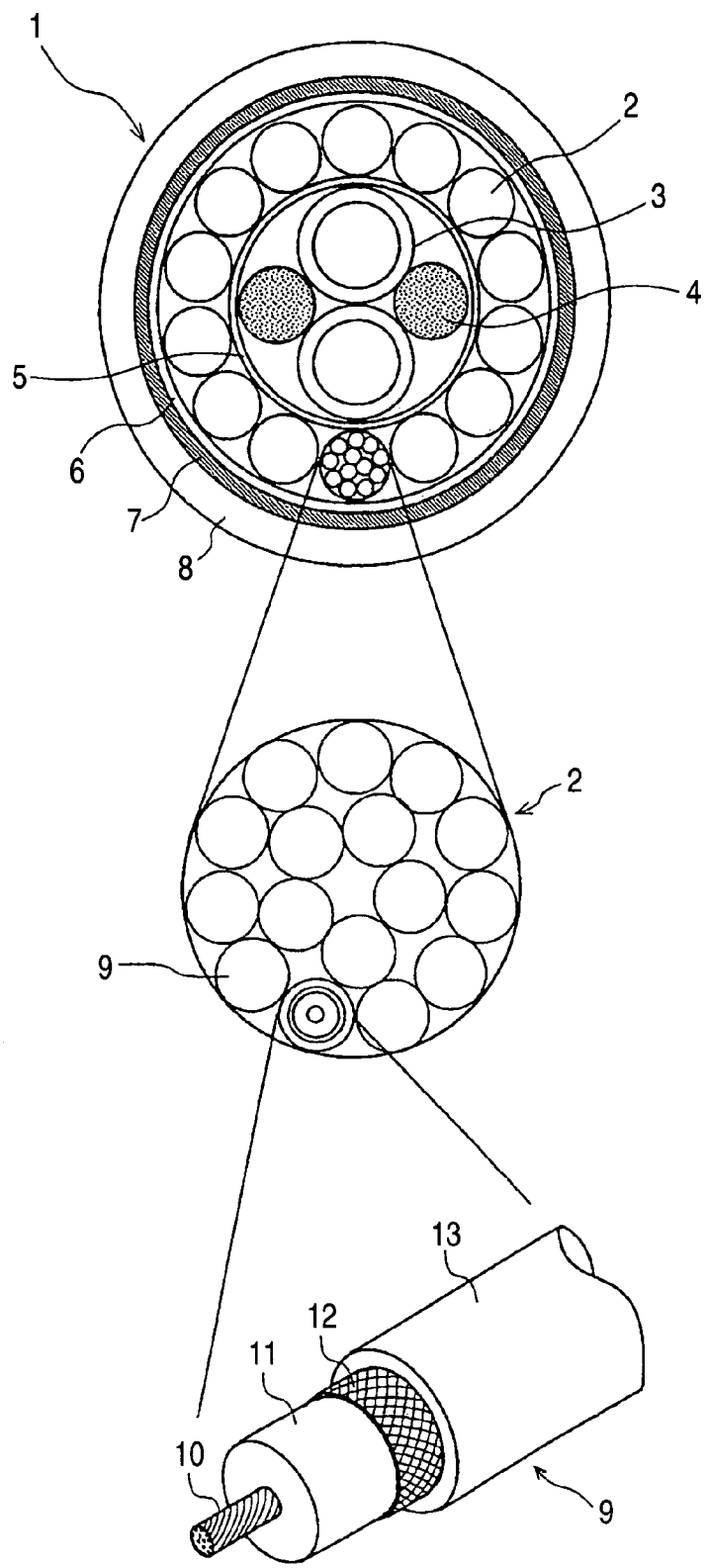
FIG. 1 is a view illustrating a composite cable according to an exemplary embodiment of the present invention.

Hereinafter, an exemplary embodiment of the invention will be explained with reference to the drawings, the following exemplary embodiment do not limit the scope of the invention. In FIG. 1, reference numeral 1 designates a composite cable, reference numeral 2 designates a signal line unit, reference numeral 3 designates a tube, reference numeral 4 designates a heat insulating member, reference numeral 5 designates a heat insulating tape, reference numeral 6 designates a wrapping tape, reference numeral 7 designates a common shield conductor, reference numeral 8 designates a cable outer jacket, reference numeral 9 designates a signal line, reference numeral 10 designates an inner conductor, reference numeral 11 designates an insulator, reference numeral 12 designates an outer conductor, and reference numeral 13 designates an insulation coating.

The composite cable 1 includes at least two tubes 3, signal line units 2 that is disposed annularly around an outer periphery of the tubes 3, and a cable outer jacket 8 that covers the tubes 3 and signal line units 2. The tubes are for permitting passages for supplying and returning refrigerant such as chlorofluorocarbons. Each of the signal line units 2 is formed by bundling a plurality of signal lines 9. For example, the signal line unit 2 may be formed by bundling two to sixteen lines of the signal lines 9, and the signal lines 9 may be wrapped and assembled with a rough winding string or a tape such that a cross section of the signal line unit 9 becomes a circular shape. The plurality of signal lines 9 may include an insulated wire for power source or a paired wire.

The signal line 9 may be an insulated wire that has no outer conductor. However, as for a device that deals with high-frequency signals, such as an ultrasonic probe, it is preferable to use a thin coaxial wire. The coaxial cable may include an inner conductor 10, an insulator 11, an outer conductor 12 and an insulation coating 13, each being aligned sequentially in a concentric manner. The inner conductor 10 may be a single wire or a twisted wire such as a copper wire or a tin-plated copper alloy wire that are high in electric conductivity. The inner conductor 10 may be formed by twisting seven lines of tin-plated copper alloy wires, each having an outer diameter of approximately 0.025 mm.

The insulator 11 is an insulating material such as Teflon (registered trademark) resin, and may be formed by tape winding or extrusion molding such that a thickness thereof becomes approximately 0.06 mm. The outer conductor 12 is used as shield by forming a tin-plated copper alloy wire having an outer diameter of approximately 0.03 mm, and the insulation coating 13 is formed by winding a plastic tape such as polyester having a thickness of approximately 0.04 mm around its outer surface, or by shaping through the use of a molding machine, and they are formed so as to become a coaxial wire having an outer diameter of approximately 0.3 mm.

As for the tubes 3 through which the refrigerant flows, at least two independent tubes 3 are employed in order to circulate the refrigerant by means of a radiator, that is, one for supplying the refrigerant and another for returning the refrigerant. The tubes 3 are made of synthetic resin that has a high flexibility, and a low thermal conductivity so that the refrigerant inside the tubes 3 does not absorb heat from outer peripheries of the tubes 3. For example, urethane resin, fluorine resin, or silicon resin may be used for the tubes 3.

The tubes 3 are assembled together with heat insulating members 4 which are made of a material that is flexible and has a low thermal conductivity, such that the heat insulating members 4 are aligned along the tubes 3, and such that an assembled outline of the tubes 3 and the heat insulating members 4 becomes close to a circular shape. Thereafter, an outer periphery of the tubes 3 and the heat insulating members 4 are wound with a heat insulating tape 5 that has a low thermal conductivity, thereby integrating the tubes 3 and the heat insulating members 4. The heat insulating tape 5 may be "a seag film". "The seag film" is a film that is used to cover windows in order to insulate an interior of a room from an exterior of the room, to prevent of a dew condensation or to protect from an ultraviolet ray. The tubes 3 may be twisted and gathered each other either alone or together with the heat insulating members 4 in case where the heat insulating members 4 are provided, and the heat insulating tape 5 may be wound around an outer periphery of the twisted and gathered tubes 3.

A plurality of signal lines 9 or a plurality of signal line units 2 may be assembled around an outer periphery of a refrigerant pipe including the tubes 3, such that the plurality of signal lines 9 or the plurality of signal line units 2 are spirally wound. The refrigerant pipe line and the plurality of signal lines 9 or the plurality of signal line units 2 are then integrated with a wrapping tape 6 such as a PTFE (polytetrafluoroethylene) resin tape. The common shield conductor 7 for all the signal lines 9 is formed around an outer periphery of the wrapping tape 6 by traverse winding or braiding copper alloy wires or copper foil strings. In this way, it becomes possible to prevent a noise from leaking outside the composite cable 1. Such a noise is caused, for example, by a friction between the signal lines 9 when the signal lines are entwined with each other by bending the composite cable 1. The cable outer jacket 8 is formed by a tape winding or an extrusion around an outer periphery of the common shield conductor 7. The cable outer jacket 8 may be made from PVC (polyvinyl chloride).

In the above-described composite cable 1, the tubes 3 for permitting the passages of the refrigerant are disposed at the central part of the composite cable 1. Accordingly, the composite cable 1 is basically the same with a normal circular cable in that they both have a unitary construction, and therefore, has an excellent handling ability with no directionality constraint with respect to a bend. The tubes 3 may be connected to a refrigerant path inside a probe so that the tube 3 for supplying the refrigerant and the tube 3 for returning the refrigerant are connected, thereby forming a single refrigerant pipe. The refrigerant is supplied through the tube 3 for supplying, and is recovered from the tube 3 for returning, whereby the refrigerant can be constantly supplied to the probe so as to cool the probe. Meanwhile, on the other end sides of the tubes 3, the high temperature refrigerant flows through a radiator to be re-cooled, and is circulated being reused.

Since the tube 3 itself is cooled by the refrigerant which runs through the tube 3, it is feared that a dew condensation is generated on a surface of the tube 3. However, according to the exemplary embodiment, the tube 3 is covered with the heat insulating tape 5, whereby the signal lines 9 that are disposed around a periphery of the tubes 3 are thermally insulated. In this way, it is possible to prevent the surrounding signal lines 9 from being adversely affected by water generating from the dew condensation, physically and electrically. Further, since the heat insulating members 4 are disposed, it is possible to wind the heat insulating tape 5 in a shape that is almost a circular shape, so that a directionality constraint with respect to a bend can be eliminated. Furthermore, since a contacting area of the heat insulating tape 5 and an outer surface of the tubes 3 is reduced, heat transfer resistance becomes high, and an amount of heat loss to an outside can be reduced.

Figure 2:
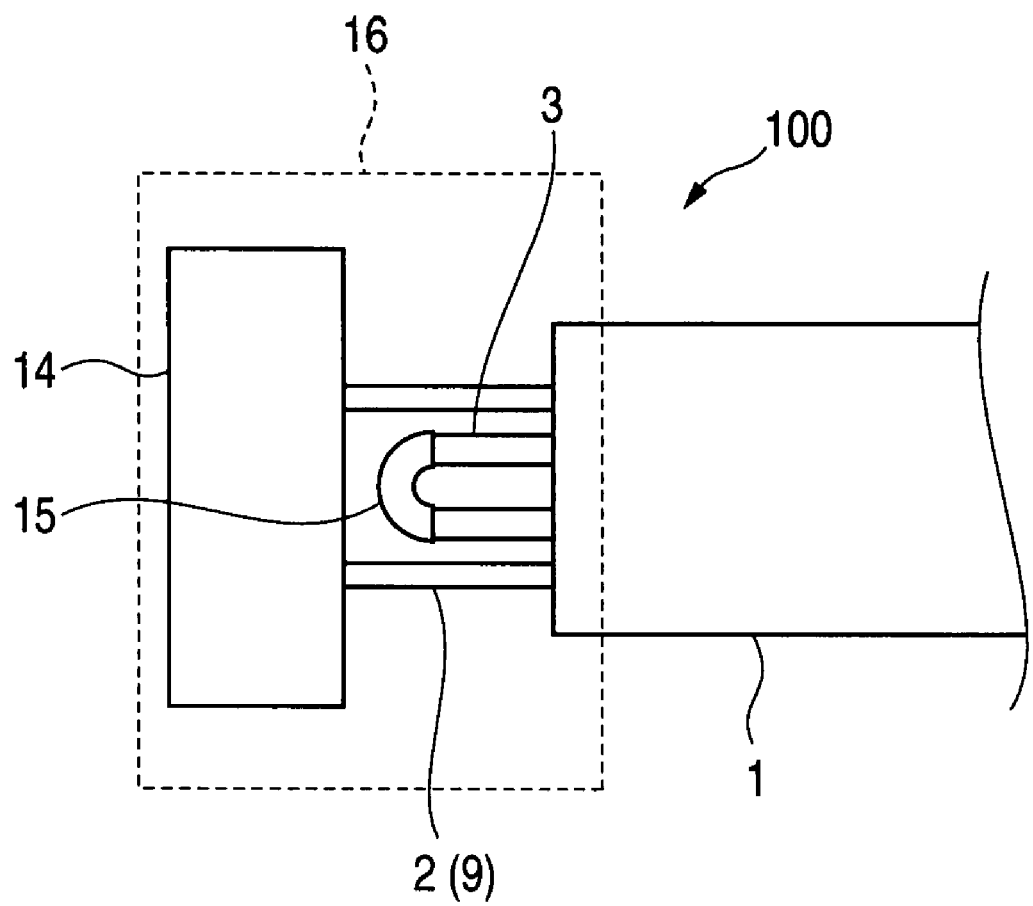
FIG. 2 is a view illustrating a composite cable processed product according to an exemplary embodiment of the present invention.

As shown in FIG. 2, when manufacturing a composite cable processed product 100, the composite cable 1 may be cut by a predetermined length, and a terminal portion of the signal lines 9 or the signal line units 2 may be connected to a component 14 such as an electric connector or a circuit substrate. In such a case, respective terminals of the tube 3 for supplying and the tube 3 for returning are coupled at a connector portion 16 via, for example, a connecting tube 15.

While description has been made in connection with exemplary embodiment of the present invention, it will be obvious to those skilled in the art that various changes and modification may be made therein without departing from the present invention. It is aimed, therefore, to cover in the appended claims all such changes and modifications falling within the true spirit and scope of the present invention.

What is claimed is:

1. A composite cable for transmitting electric signals from an ultrasonic probe, the composite cable comprising:
   at least two flexible resin tubes through which a refrigerant flows;
   heat insulating members which are aligned along the resin tubes such that an assembled outline of the tubes and the heat insulating members becomes close to a circular shape;
   a heat insulating tape that is wound around an outer periphery of the resin tubes and the heat insulating members; and
   a plurality of signal lines or a plurality of signal line units, each signal line unit including a plurality of signal lines,
   wherein the plurality of signal lines or the plurality of signal line units is disposed annularly around the heat insulating tape.

2. The composite cable according to claim 1, further comprising:
   a wrapping tape; and
   a common shield conductor,
   wherein the plurality of signal lines or the plurality of signal line units is assembled around the resin tubes, and is wrapped with the wrapping tape, and
   the common shield conductor is formed around an outer periphery of the wrapping tape.

3. The composite cable according to claim 1, further comprising:
   a wrapping tape; and
   a common shield conductor,
   wherein the plurality of signal lines or the plurality of signal line units is assembled around the heat insulating tape, and is wrapped with the wrapping tape, and
   the common shield conductor is formed around an outer periphery of the wrapping tape.

4. A composite cable processed product comprising:
   the composite cable according to claim 1; and
   a component,
   wherein the plurality of signal lines or the plurality of signal line units is connected to the component at a terminal portion of the composite cable, and
   at least two of the resin tubes are coupled at the terminal portion of the composite cable.

5. The composite cable processed product according to claim 4, wherein the component includes an electric connector.

6. The composite cable processed product according to claim 4, wherein the component includes a circuit substrate.

7. The composite cable processed product according to claim 4, further comprising a connecting tube, wherein at least two of the resin tubes are coupled at the terminal portion of the composite cable via the connecting tube.

* * * * *